(12) United States Patent
Watson et al.

(10) Patent No.: US 8,385,675 B2
(45) Date of Patent: Feb. 26, 2013

(54) SYSTEMS AND METHODS FOR FILTERING A SIGNAL USING A CONTINUOUS WAVELET TRANSFORM

(75) Inventors: James Nicholas Watson, Dunfermline (GB); Paul Stanley Addison, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 713 days.

(21) Appl. No.: 12/249,100

(22) Filed: Oct. 10, 2008

(65) Prior Publication Data

US 2010/0014725 A1   Jan. 21, 2010

Related U.S. Application Data

(60) Provisional application No. 61/080,833, filed on Jul. 15, 2008.

(51) Int. Cl.
*G06K 9/40* (2006.01)
*H04B 15/00* (2006.01)
*H04N 5/00* (2011.01)

(52) U.S. Cl. .......................... 382/261; 702/191; 348/607
(58) Field of Classification Search .................... 382/261
See application file for complete search history.

(56) References Cited

U.S. PATENT DOCUMENTS

| | | | |
|---|---|---|---|
| 4,289,141 A | 9/1981 | Cormier | |
| 5,439,483 A | 8/1995 | Duong-Van | |
| 5,482,036 A | 1/1996 | Diab et al. | |
| 5,490,505 A | 2/1996 | Diab et al. | |
| 5,590,650 A | 1/1997 | Genova | |
| 5,632,272 A | 5/1997 | Diab et al. | |
| 5,671,264 A * | 9/1997 | Florent et al. | 378/98 |
| 5,685,299 A | 11/1997 | Diab et al. | |
| 5,769,785 A | 6/1998 | Diab et al. | |
| 5,778,881 A | 7/1998 | Sun et al. | |
| 5,795,304 A | 8/1998 | Sun et al. | |
| 5,797,840 A | 8/1998 | Akselrod et al. | |
| 5,827,195 A | 10/1998 | Lander | |
| 5,924,980 A | 7/1999 | Coetzee | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey et al. | |

(Continued)

FOREIGN PATENT DOCUMENTS

| | | |
|---|---|---|
| JP | 09-084776 | 3/1997 |
| WO | WO 01/25802 | 4/2001 |

(Continued)

OTHER PUBLICATIONS

Addison, Paul S., The Illustrated Wavelet Transform Handbook, Taylor & Francis Group, 2002.

(Continued)

*Primary Examiner* — David Zarka

(57) ABSTRACT

According to embodiments, systems and methods for reducing noise in a signal are provided. A signal may be transformed using a continuous wavelet transform and a corresponding scalogram may be generated. Regions of noise may be identified from the resulting scalogram. These regions may be masked by, for example, removing, altering, or appropriately tagging the regions. After masking the regions of noise, the scalogram may be converted to a filtered signal using an inverse wavelet transform. Alternatively or additionally, desirable regions of non-noise may instead be identified from the resulting scalogram. These desirable regions may be extracted from the scalogram and an inverse wavelet transform performed on the extracted regions in order to generate a filtered signal.

18 Claims, 13 Drawing Sheets

U.S. PATENT DOCUMENTS

| | | | |
|---|---|---|---|
| 6,095,984 A | 8/2000 | Amano et al. | |
| 6,117,075 A | 9/2000 | Barnea | |
| 6,129,675 A | 10/2000 | Jay | |
| 6,135,952 A | 10/2000 | Coetzee | |
| 6,135,966 A | 10/2000 | Ko | |
| 6,171,257 B1 | 1/2001 | Weil et al. | |
| 6,171,258 B1 | 1/2001 | Karakasoglu et al. | |
| 6,206,830 B1 | 3/2001 | Diab et al. | |
| 6,208,951 B1 * | 3/2001 | Kumar et al. | 702/191 |
| 6,253,175 B1 * | 6/2001 | Basu et al. | 704/231 |
| 6,263,222 B1 | 7/2001 | Diab et al. | |
| 6,293,915 B1 | 9/2001 | Amano et al. | |
| 6,325,761 B1 | 12/2001 | Jay | |
| 6,359,658 B1 * | 3/2002 | He et al. | 348/607 |
| 6,361,501 B1 | 3/2002 | Amano et al. | |
| 6,393,311 B1 | 5/2002 | Edgar, Jr. et al. | |
| 6,501,975 B2 | 12/2002 | Diab et al. | |
| 6,561,986 B2 | 5/2003 | Baura | |
| 6,608,934 B2 | 8/2003 | Scheirer | |
| 6,654,623 B1 | 11/2003 | Kastle | |
| 6,810,277 B2 | 10/2004 | Edgar, Jr. et al. | |
| 6,826,419 B2 | 11/2004 | Diab et al. | |
| 6,826,513 B1 * | 11/2004 | Kumar et al. | 702/185 |
| 6,931,269 B2 | 8/2005 | Terry | |
| 6,961,742 B2 | 11/2005 | Neretti et al. | |
| 7,001,337 B2 | 2/2006 | Dekker | |
| 7,020,507 B2 | 3/2006 | Scharf | |
| 7,031,548 B2 * | 4/2006 | Baggs | 382/261 |
| 7,035,679 B2 * | 4/2006 | Addison et al. | 600/323 |
| 7,043,293 B1 | 5/2006 | Baura | |
| 7,054,453 B2 | 5/2006 | Causevic et al. | |
| 7,054,454 B2 | 5/2006 | Causevic et al. | |
| 7,079,888 B2 | 7/2006 | Oung | |
| 7,167,746 B2 | 1/2007 | Pederson | |
| 7,171,269 B1 * | 1/2007 | Addison et al. | 607/7 |
| 7,173,525 B2 | 2/2007 | Albert | |
| 7,203,267 B2 | 4/2007 | De Man et al. | |
| 7,225,013 B2 | 5/2007 | Geva et al. | |
| 7,254,500 B2 | 8/2007 | Makeig | |
| 7,289,835 B2 | 10/2007 | Mansfield | |
| 7,515,949 B2 | 4/2009 | Norris | |
| 7,519,488 B2 | 4/2009 | Fu | |
| 7,523,011 B2 | 4/2009 | Akiyama et al. | |
| 2003/0163057 A1 | 8/2003 | Flick et al. | |
| 2005/0043616 A1 | 2/2005 | Chinchoy | |
| 2005/0043763 A1 | 2/2005 | Marcovecchio et al. | |
| 2006/0209631 A1 | 9/2006 | Melese et al. | |
| 2006/0229519 A1 | 10/2006 | Fujiwara et al. | |
| 2006/0258921 A1 | 11/2006 | Addison et al. | |
| 2006/0265022 A1 | 11/2006 | John et al. | |
| 2007/0021673 A1 | 1/2007 | Arbel et al. | |
| 2007/0073120 A1 | 3/2007 | Li et al. | |
| 2007/0073124 A1 | 3/2007 | Li et al. | |
| 2007/0167694 A1 | 7/2007 | Causevic et al. | |
| 2007/0167851 A1 | 7/2007 | Vitali et al. | |
| 2007/0282212 A1 | 12/2007 | Sierra et al. | |
| 2008/0045832 A1 | 2/2008 | McGrath | |
| 2008/0082018 A1 | 4/2008 | Sackner et al. | |
| 2008/0214903 A1 | 9/2008 | Orbach | |
| 2008/0243021 A1 | 10/2008 | Causevic et al. | |
| 2009/0326871 A1 * | 12/2009 | Watson et al. | 702/191 |
| 2010/0014723 A1 * | 1/2010 | Addison et al. | 382/128 |
| 2010/0016676 A1 * | 1/2010 | Addison et al. | 600/300 |
| 2010/0016696 A1 * | 1/2010 | Addison et al. | 600/331 |

FOREIGN PATENT DOCUMENTS

| | | |
|---|---|---|
| WO | WO 01/62152 | 8/2001 |
| WO | WO 01/82099 | 11/2001 |
| WO | WO 03/000125 | 1/2003 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Yamada, Michio, "Wavelet Analysis and Its Application," Journal of the Institute of Electronics, Information and Communication Engineers, vol. 76, No. 5, May 1993, pp. 518-528.

* cited by examiner

SYSTEMS AND METHODS FOR FILTERING A SIGNAL USING A CONTINUOUS WAVELET TRANSFORM

CROSS-REFERENCE TO RELATED APPLICATIONS

This claims the benefit of U.S. Provisional Application No. 61/080,833, entitled "Systems and Methods for Reducing Noise in a Signal Using a Continuous Wavelet Transform," filed Jul. 15, 2008, which is hereby incorporated by reference herein in its entirety,

SUMMARY

The present disclosure relates to signal processing and, more particularly, to using a continuous wavelet transform for filtering noise in signals such as, for example, a photoplethysmograph (PPG) signal.

The advantages of the Continuous Wavelet Transform (CWT), such as inherent resolution in both scale and time, may be used to identify and characterize features within an input signal. The regions and amplitudes within the scalogram associated with these features may then be isolated and extracted and used to produce a filtered signal for future use. For example, in some embodiments, the filtered signal may be generated by removing undesirable features from the input signal and then performing an inverse wavelet transform. As another example, desired data may be extracted from the input signal and an inverse wavelet transform performed on this desired data to generate the filtered signal.

For example, after a continuous wavelet transform has been performed on the input signal, a scalogram of the transformed signal may be generated. Undesirable artifacts in the original signal may be identified in the scalogram through, for example, the artifact's abnormal shape and energy density with respect to its surroundings. The amplitudes associated with this feature may then be removed or altered from the input signal. This may result in a filtered signal that is the input signal with some or all of the artifacts removed. An inverse CWT may then be performed on the filtered signal.

As another example, desired data may be identified in the scalogram. For example, in a PPG signal, physiological parameters such as pulse rate, respiration rate, etc. may be identified. This desired data may then be extracted, and this extracted data used to generate the filtered signal. Once again, an inverse CWT may then be performed on the filtered signal.

This method may also optionally be used in combination with other techniques, including conventional techniques such as Kalman filtering. For example the signal may be pre-filtered using Kalman filters prior to being wavelet filtered. This may produce improved performance.

BRIEF DESCRIPTION OF THE DRAWINGS

The above and other features of the present disclosure, its nature and various advantages will be more apparent upon consideration of the following detailed description, taken in conjunction with the accompanying drawings, in which like reference characters refer to like parts throughout, and in which.

DETAILED DESCRIPTION

Figure 1:
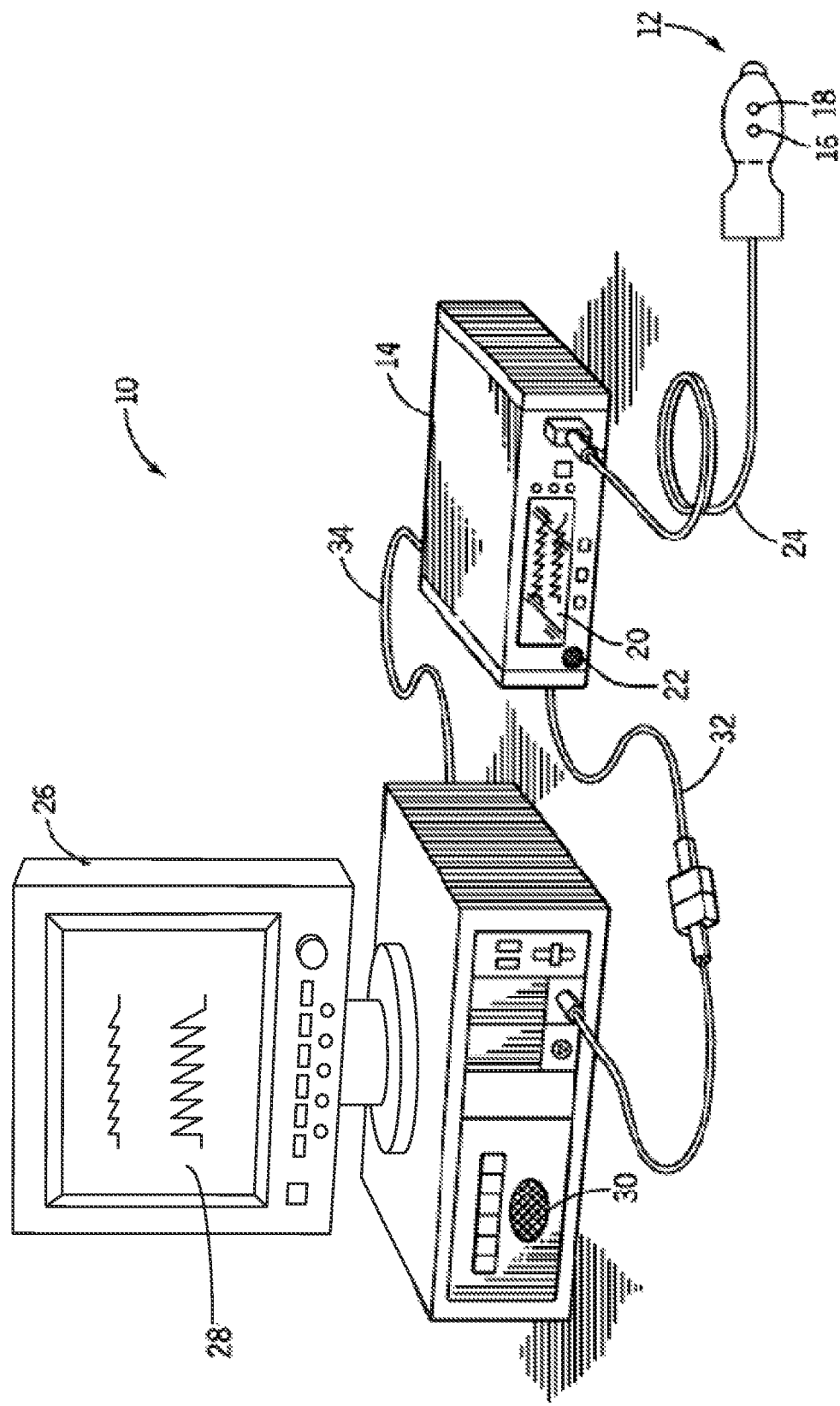
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patients blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead, or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time may be referred to as the photoplethysmogram (PPG) signal. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:

λ=wavelength;

t=time;

I=intensity of light detected;

$I_o$=intensity of light transmitted;

s=oxygen saturation;

$\beta_o$, $\beta_r$=empirically derived absorption coefficients; and l(t)=a combination of concentration and path length from emitter to detector as a function of time.

The traditional approach measures light-absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red wavelengths:

$$\log I = \log I_o - (s\beta_o + (1-s)\beta_r)l \quad (2)$$

2. (2) is then differentiated with respect to time:

$$\frac{d\log I}{dt} = -(s\beta_o + (1-s)\beta_r)\frac{dl}{dt} \quad (3)$$

3. Red (3) is divided by IR (3):

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s:

$$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time:

$$\frac{d\log I(\lambda, t)}{dt} \simeq \log I(\lambda, t_2) - \log I(\lambda, t_1)$$

Using log A−log B=log A/B:

$$\frac{d\log I(\lambda, t)}{dt} \simeq \log\left(\frac{I(t_2, \lambda)}{I(t_1, \lambda)}\right)$$

So, (4) can be rewritten as:

$$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives:

$$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship:

$$\frac{d\log I}{dt} = \frac{dI/dt}{I} \quad (6)$$

now (5) becomes:

$$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where:

$$x(t) = [I(t_2, \lambda_{IR}) - I(t_1, \lambda_{IR})]I(t_1, \lambda_R) \quad y(t) = [I(t_2, \lambda_R) - I(t_1, \lambda_R)]I(t_1, \lambda_{IR}) \quad y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14, and blood pressure from a blood pressure monitor (not shown) on display 28. Monitor 26 may also include speaker 30 that may be, for example similar to speaker 22 of monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
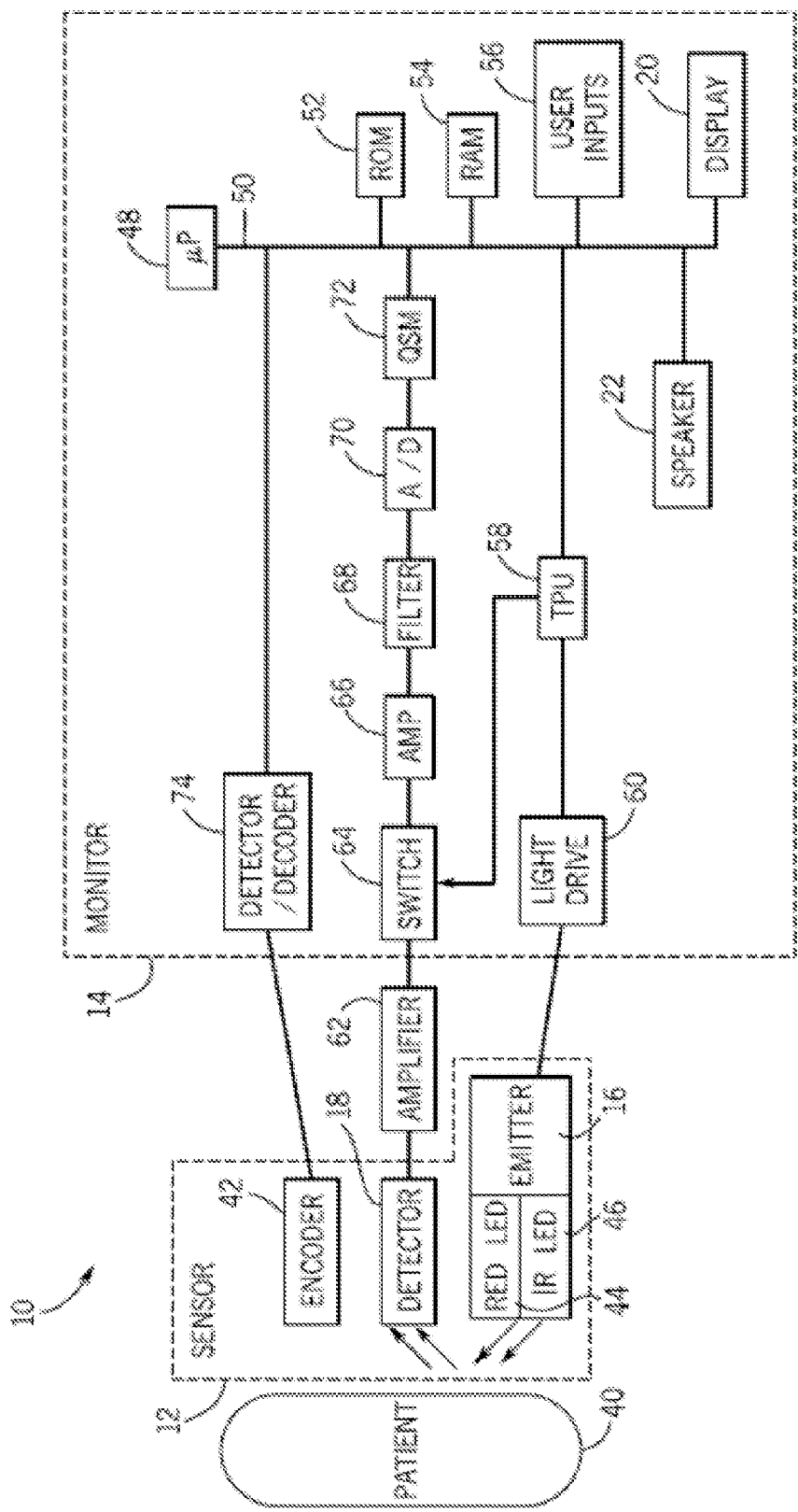
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less or more light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet-space) may be used to provide measurements of one or more physiological parameters.

The continuous wavelet transform of a signal x(t) in accordance with the present disclosure may be defined as:

$$T(a, b) = \frac{1}{\sqrt{a}} \int_{-\infty}^{+\infty} x(t)\psi^*\left(\frac{t-b}{a}\right) dt \quad (9)$$

where $\psi^*(t)$ is the complex conjugate of the wavelet function $\psi y(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet-space includes a time dimension, spectral techniques and wavelet techniques are not interchangeable. It will be understood that converting a system that relies on spectral domain processing to one that relies on wavelet-space processing would require significant and fundamental modifications to the system in order to accommodate the wavelet-space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as:

$$S(a,b)=|T(a,b)|^2 \quad (10)$$

where '||' is the modulus operator. The scalogram may be resealed for useful purposes. One common resealing is defined as:

$$S_R(a, b) = \frac{|T(a, b)|^2}{a} \quad (11)$$

and is useful for defining ridges in wavelet-space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by:

$$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{i2\pi f_0 t}-e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as:

$$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
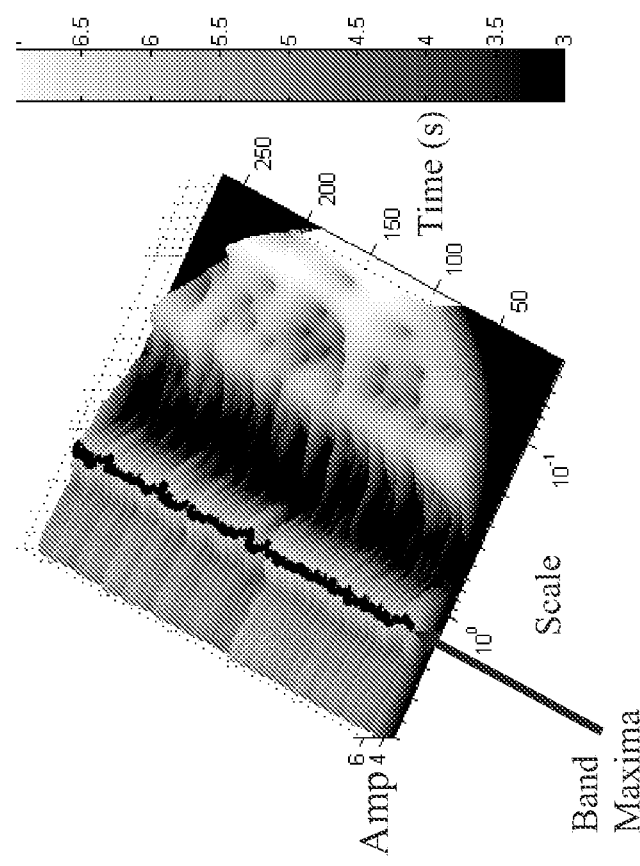
FIGS. 3(a) and 3(b) show illustrative views of a scalogram derived from a PPG signal in accordance with an embodiment.
Figure 3A:
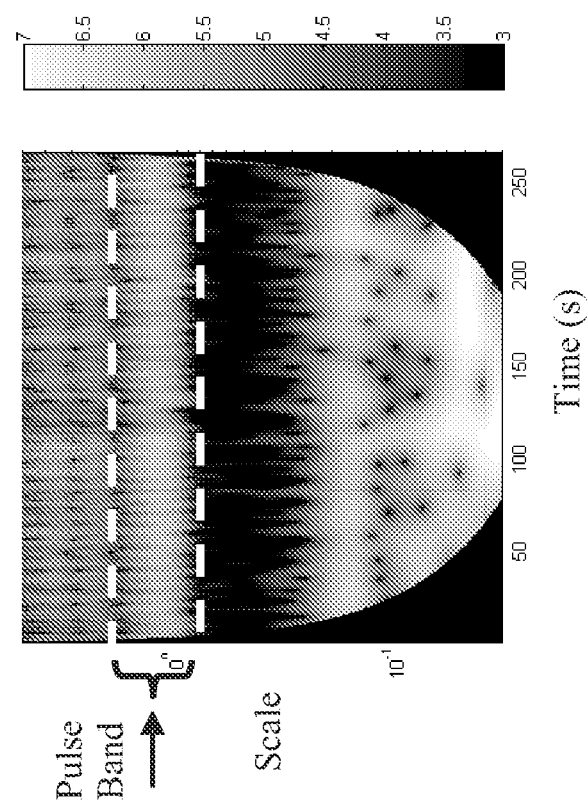

Pertinent repeating features in a signal give rise to a time-scale band in wavelet-space or a resealed wavelet-space. For example, the pulse component of a PPG signal produces a dominant band in wavelet-space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet-space may be related to the instantaneous frequency of the signal. In this way) the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
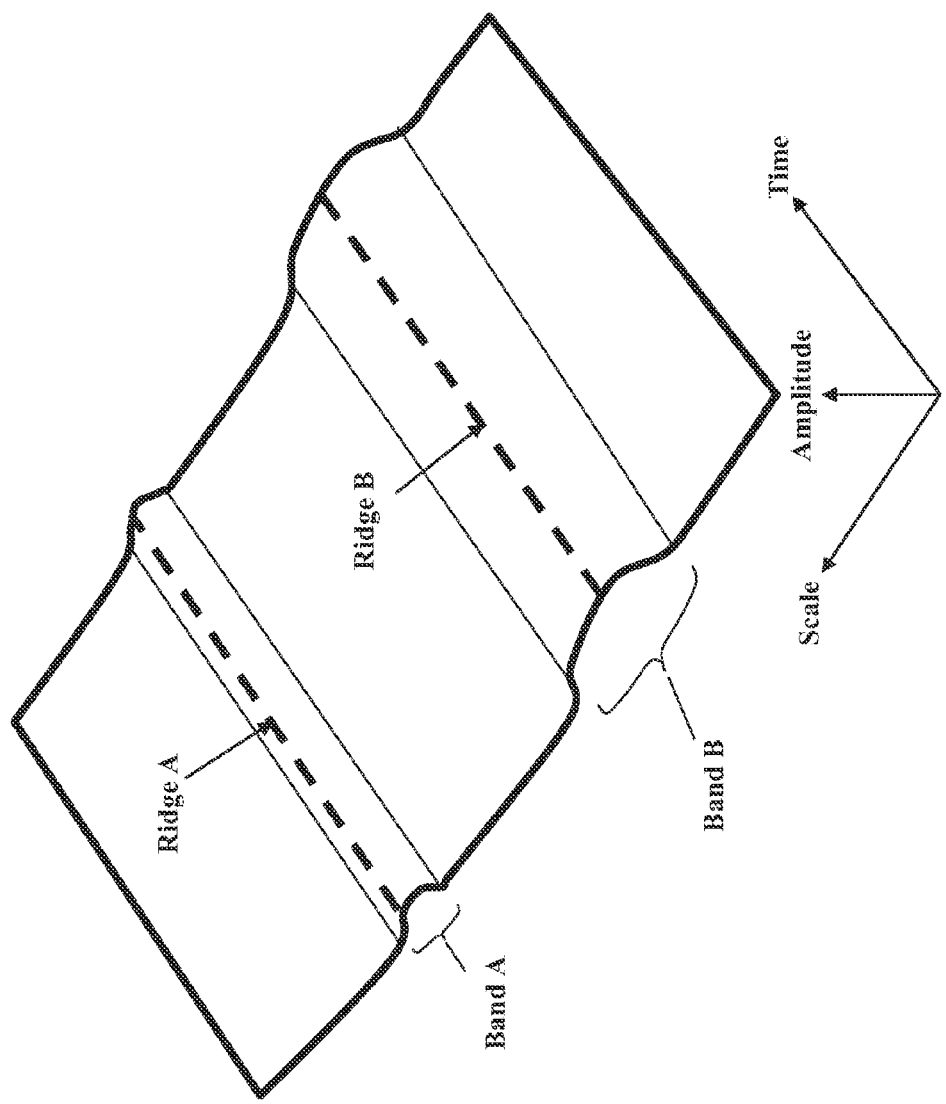
FIG. 3(c) shows an illustrative scalogram derived from a signal containing two pertinent components in accordance with an embodiment.
Figure 3D:
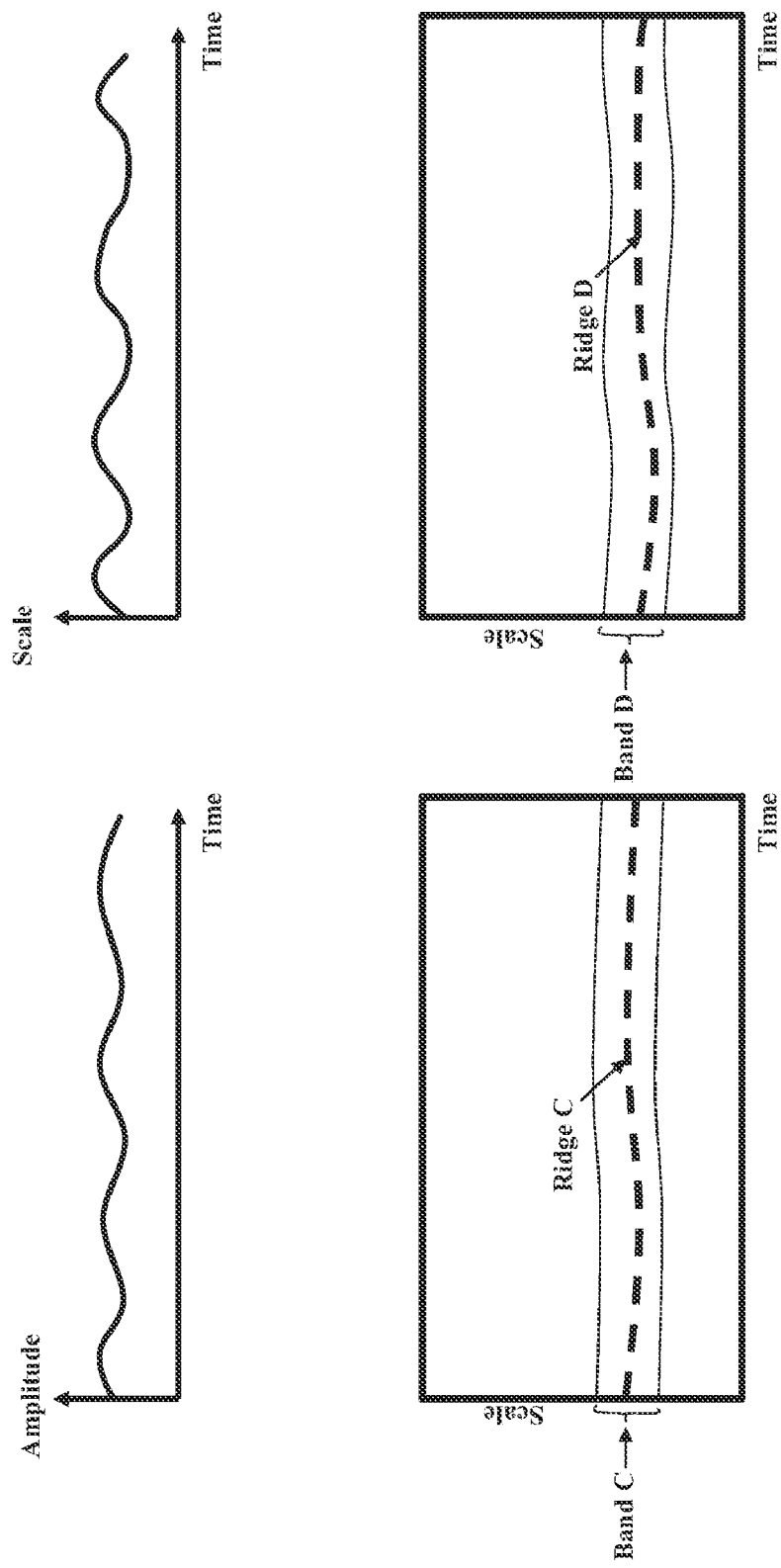
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet-space or a resealed wavelet-space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet-space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which wilt be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
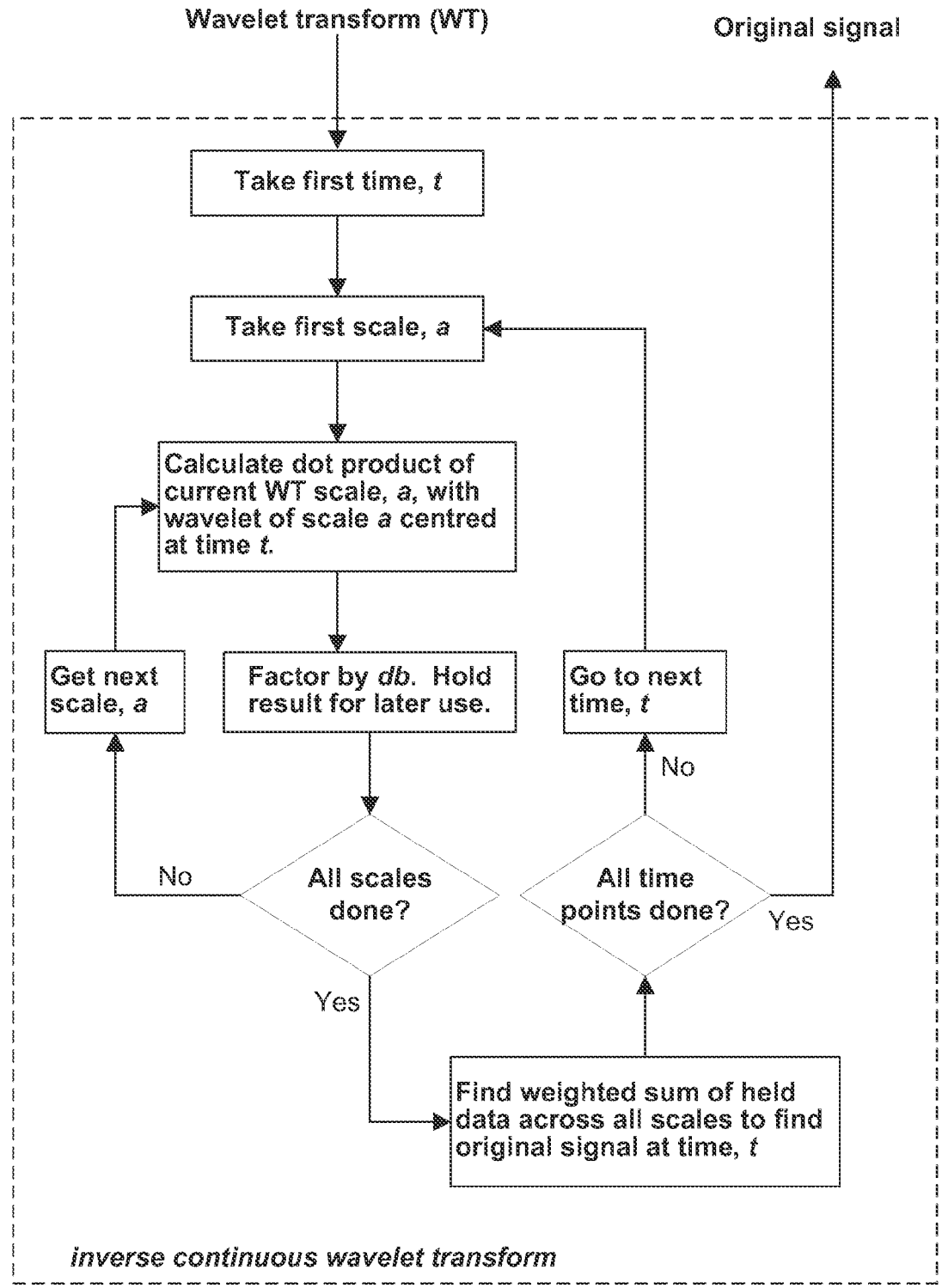
FIGS. 3(e) and 3(i) are flow charts of illustrative steps involved in performing an inverse continuous wavelet transform in accordance with an embodiment.
Figure 3F:
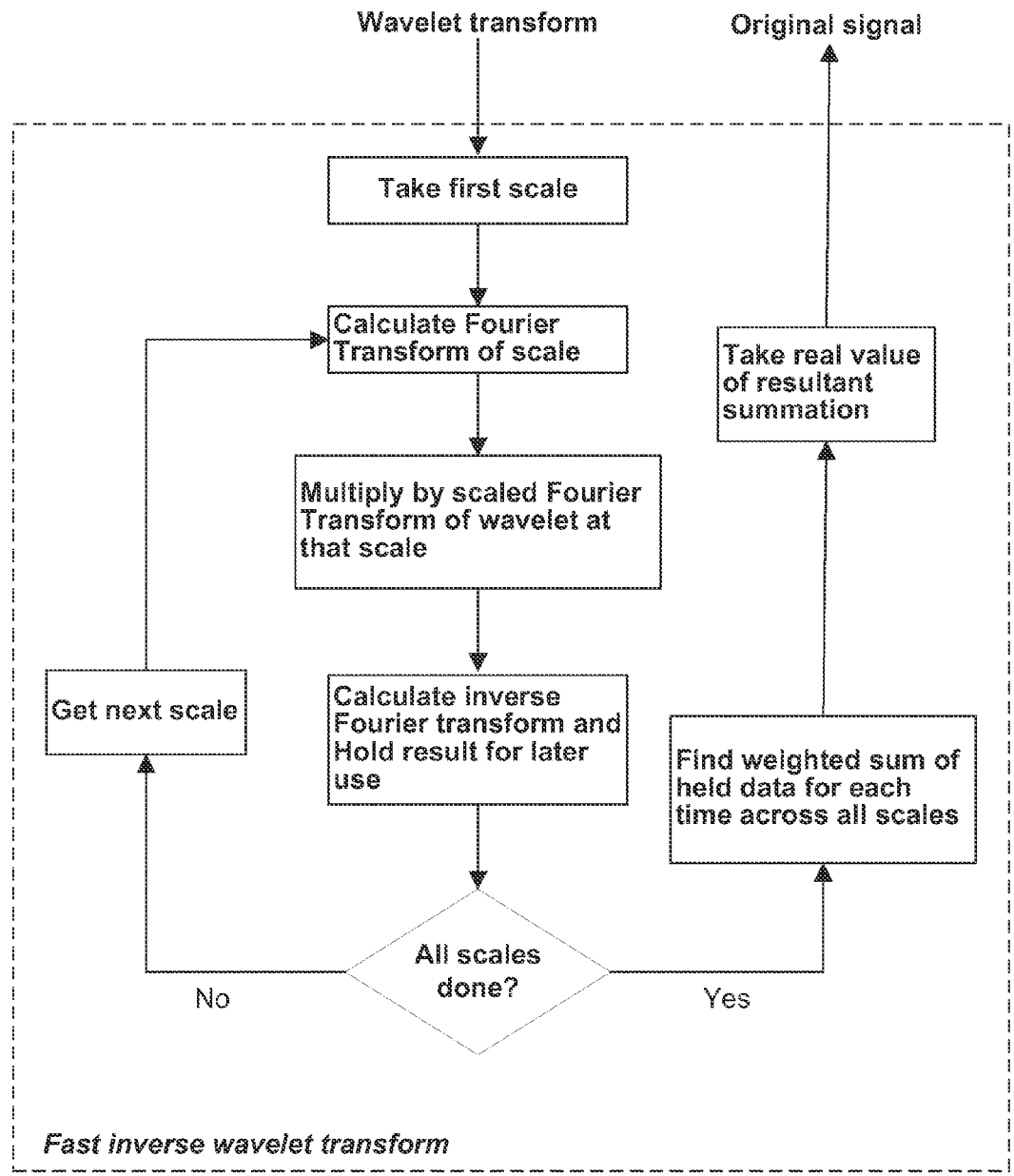

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
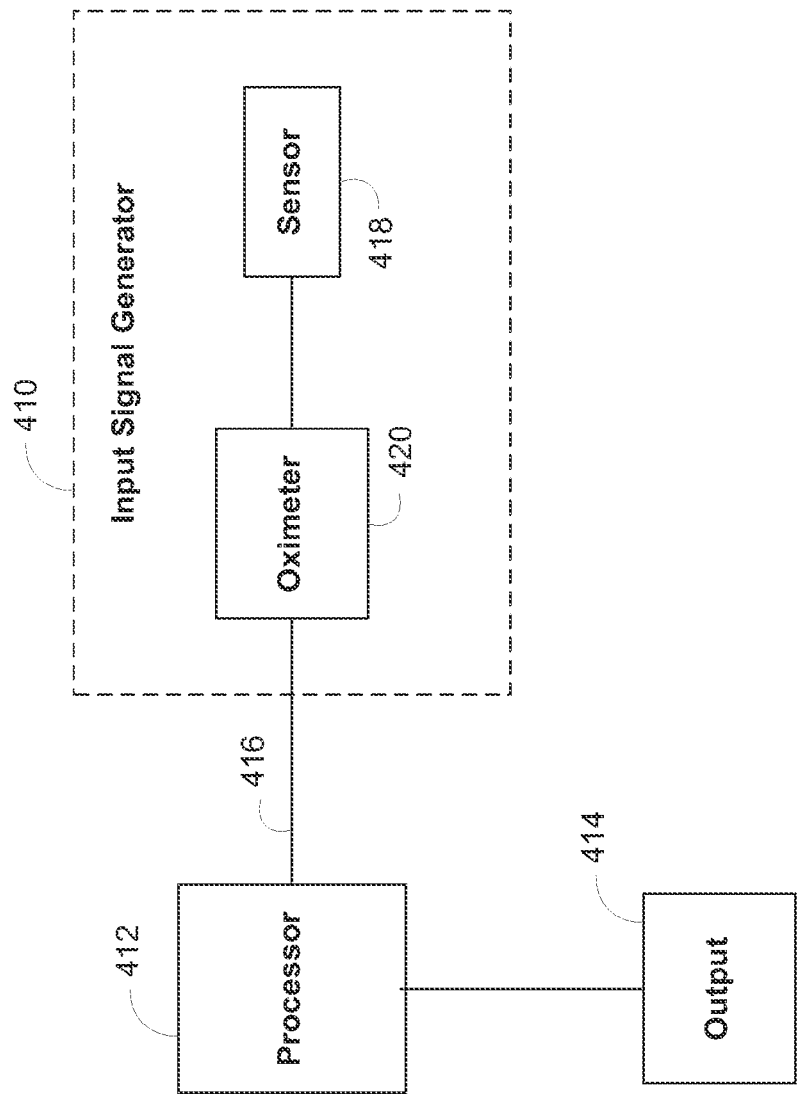
FIG. 4 is a block diagram of an illustrative continuous wavelet processing system in accordance with an embodiment.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Signals, such as PPG signals, typically contain noise due to any of a multitude of sources such as environmental factors, motion-induced noise, interference from equipment, cables, etc. The term noise used herein may refer to any undesired component or portion of a signal. In one embodiment, noise in a signal may be filtered using a continuous wavelet transform of the signal.

Figure 5:
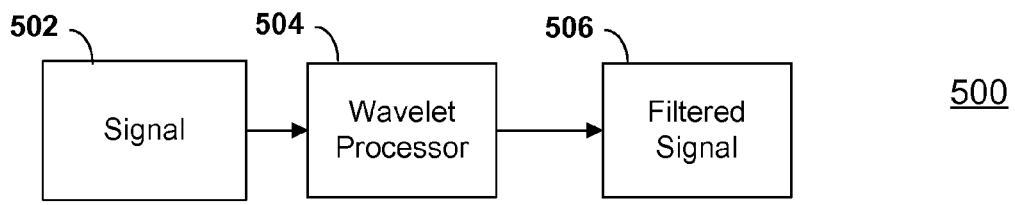
FIG. 5 shows an illustrative system that may be utilized to filter noise in accordance with an embodiment.

For example, system 500 of FIG. 5 generally illustrates a system that may be utilized to filter noise in input signal 502. For example, input signal 502 may be input signal 416 of FIG. 4. Wavelet processor 504 may then receive input signal 502, for example, through a sensor, such as sensor 12 of FIG. 2. In some embodiments, wavelet processor 504 may perform the calculations associated with the continuous wavelet transforms of the present disclosure as well as the calculations associated with any suitable interrogations of the transforms. For example, wavelet processor 504 may perform any suitable signal processing of input signal 502, such as any suitable band-pass filtering, adaptive filtering, closed-loop filtering, and/or any other suitable filtering, and/or any combination thereof. Wavelet processor 504 may be, for example, processor 412 of FIG. 4.

Wavelet processor 504 may then generate a filtered signal 506 from input signal 502. In an embodiment, filtered signal 506 may be generated by removing components from input signal 502 (e.g., by removing components from a scalogram derived from input signal 502) and then performing an inverse continuous wavelet transform on the remaining portion of input signal 502. For example, noise may be removed from input signal 502 and then an inverse transformed performed. In another embodiment, filtered signal 506 may be generated by extracting desirable data from input signal 502 (e.g., extracting data from a scalogram derived from input signal 502) and then performing an inverse wavelet transform on the extracted data. For example, in a PPG signal, physiological parameters such as pulse rate, respiration rate, etc. may be extracted from the input signal. An inverse continuous wavelet transform may then be performed on the extracted, desirable data in order to generate filtered signal 506.

Figure 6:
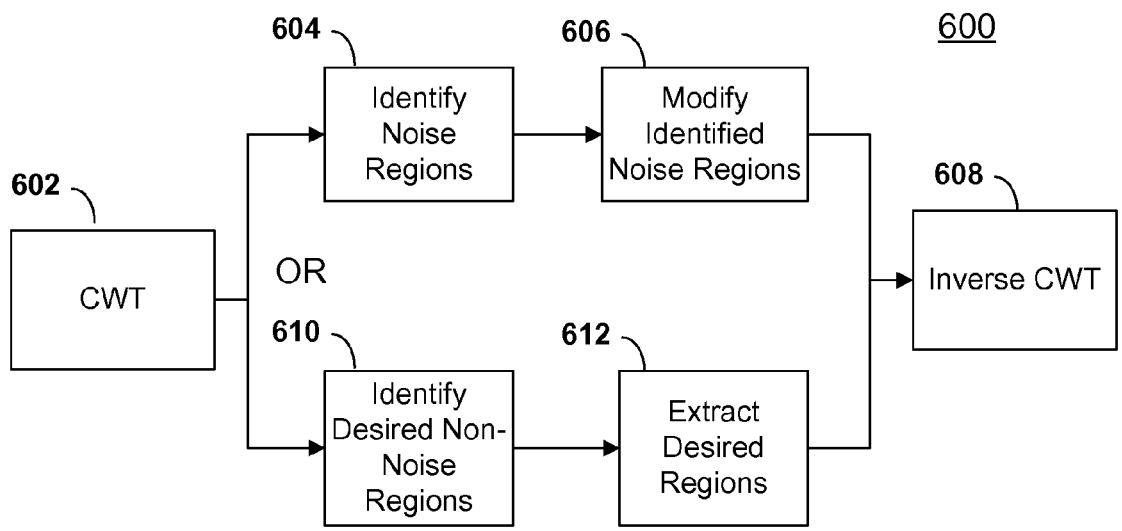
FIG. 6 shows an illustrative process for generating a filtered signal from an input signal in accordance with an embodiment.

FIG. 6 illustrates process 600 which wavelet processor 504 may perform in order to generate a filtered signal from an input signal, such as input signal 416 of FIG. 4. In step 602, one or more continuous wavelet transforms of the input signal may be created in accordance with the present disclosure for generating scalograms. For example, in an embodiment, a scalogram may be created by performing the continuous wavelet transform given by equation (9) on the input signal and then performing equation (10) to generate a scalogram or equation (11) to generate a resealed scalogram.

In step 604, as described in more detail below, noise in regions of the scalogram may be identified. A similar approach for identifying noise is described in U.S. patent application Ser. No. 12/245,336, entitled "SYSTEMS AND METHODS FOR ARTIFACT DETECTION IN SIGNALS," filed on Oct. 3, 2008, which is hereby incorporated by reference in its entirety.

In an embodiment, in order to detect regions of noise, selected areas (typically a "wedge" shaped area) of the wavelet-space may be probed. To probe the selected areas, the energy per unit time (power) in a sliding-wedge window region is defined as:

$$P_w(t) = \int_{a_{min}}^{a_{max}} \frac{\left[\int_{t-ka}^{t+ka} \frac{|T(a,b)|^2}{a^2 C_g} db\right]}{2ka} da; \tag{18}$$

where the wedge width 2 ka is defined in terms of a multiple of scale and k is an arbitrary constant. The resulting wedge power signal, $P_w(t)$, may then be compared to a threshold value. Wavelet processor 504 may then identify noise regions as those segments of $P_w(t)$ where the wedge power signal increases beyond the threshold value. Although the remaining discussion will refer to the wedge power signal, additional power signals can be used for detecting regions of noise, such as, for example, a power signal derived from the pulse ridge amplitude in resealed wavelet-space or a localized signal power measure. These power signals are also discussed in U.S. patent application Ser. No. 12/245,336, filed on Oct. 3, 2008, which is hereby incorporated by reference in its entirety.

In some embodiments, the threshold value may simply be a pre-determined value. In other embodiments, the threshold may be based on the previously detected energy measurements (e.g., a running or moving average of previously detected energy measurements) thus creating a "moving" threshold. Furthermore, additional robustness and accuracy may be created for the moving threshold by computing the moving threshold using values from the wedge power signal that are a combination of both a local component and a global component. For example, the local component may be derived from the wedge power signal over a short window (e.g., 10 seconds), and the global component may be derived over a longer window (e.g., 60 seconds). Using both components may allow the moving threshold to more accurately account for, for example, regions where multiple movements occur over a period beyond the local window (which may otherwise increase the moving threshold by some order of magnitude, thus resulting in undetected noise) or regions of near zero power (which may otherwise set the moving threshold too low).

In step 606, a scalogram mask may be created (e.g., created by wavelet processor 504) to mask the regions of noise that were identified in step 604. By masking the identified noise regions, the identified noise regions may be filtered, zeroed out, smoothed, replaced, marked for later processing, ignored, or otherwise modified. For example, in an embodiment, regions of a scalogram identified as noise may be removed from the scalogram or replaced with zero-values. As another example, in some embodiments, the noise region may be smoothed by removing the noise region and then creating "side skirts" around the noise region (e.g., generally, exponentially decaying side boundaries extending out on one or both sides an identified noise region). In some embodiments, if there is generally a repeating signal near the noise region, the noise region may be smoothed in a manner which allows the repeating signal to be present in the noise region after the noise region has been smoothed.

Alternatively, regions of a scalogram that are not to be removed from the filtered signal (e.g., filtered signal 506 of FIG. 5) may be suitably marked or tagged in step 606 such that when an inverse continuous wavelet transform is performed, the marked or tagged bands of scales may be ignored, suppressed, or altered (e.g., regions may be altered with respect to their context) to generate the filtered signal. For example, areas of a noise region may be marked and then later ignored in the computation of a parameter (e.g., a physiological parameter) derived from the scalogram. The scalogram may be further parameterized by the loci of its local maxima and their subsets such as ridges and modulus maxima (e.g., maximal turning points along scales across time). These loci, particularly the modulus maxima, may be particularly useful for filtering the signal of temporally localized artifact, for example spikes. For particular wavelets, such as those that are derivatives of a Gaussian function, a signal may be reconstructed from the modulus maxima of its wavelet transform.

Rather than identifying noise components of the scalogram in step 604, in some embodiments, process 600 may alternatively or additionally proceed to step 610 after performing a continuous wavelet transform of the input signal in step 602. In step 610, desirable, non-noise regions of the scalograms may be identified. In the context of PPG signals, for example, a scalogram generated from a continuous wavelet transform of a PPG signal generally contains a band of scales corresponding to the pulse components of the PPG signal and a band of scales corresponding to the breathing components of the PPG signal, both of which may be desirable, non-noise components of the input signal. Additionally, regions representative of other, natural physiological operations and parameters may be contained on the scalogram. These components, as well as any one or more other regions that do not correspond to noise, may be identified in step 610 as desirable regions of the scalogram.

After identifying desirable regions of the scalogram in step 610, process 600 may then proceed to step 612. In step 612, the desirable regions of the scalogram are extracted. These extracted regions may then be used to generate the filtered signal.

After either step 606 or step 612, process 600 may proceed to step 608. In step 608, an inverse continuous wavelet transform may be performed on the masked signal or extracted regions in order to produce a filtered signal (e.g., filtered signal 506 of FIG. 5). For example, an inverse continuous wavelet transform, such as equation (15), may be used to produce the filtered signal. In some embodiments, the inverse transform and step 608 may be unnecessary. For example, if further operations with the filtered scalogram or signal are to be performed in wavelet-space, it may be desirous not to perform the inverse continuous wavelet transform and to instead allow the masked signal or extracted regions to remain in wavelet-space. In this scenario, rather than being a signal in time-space, the filtered signal may be considered the masked signal or extracted data in wavelet-space.

Figure 7:
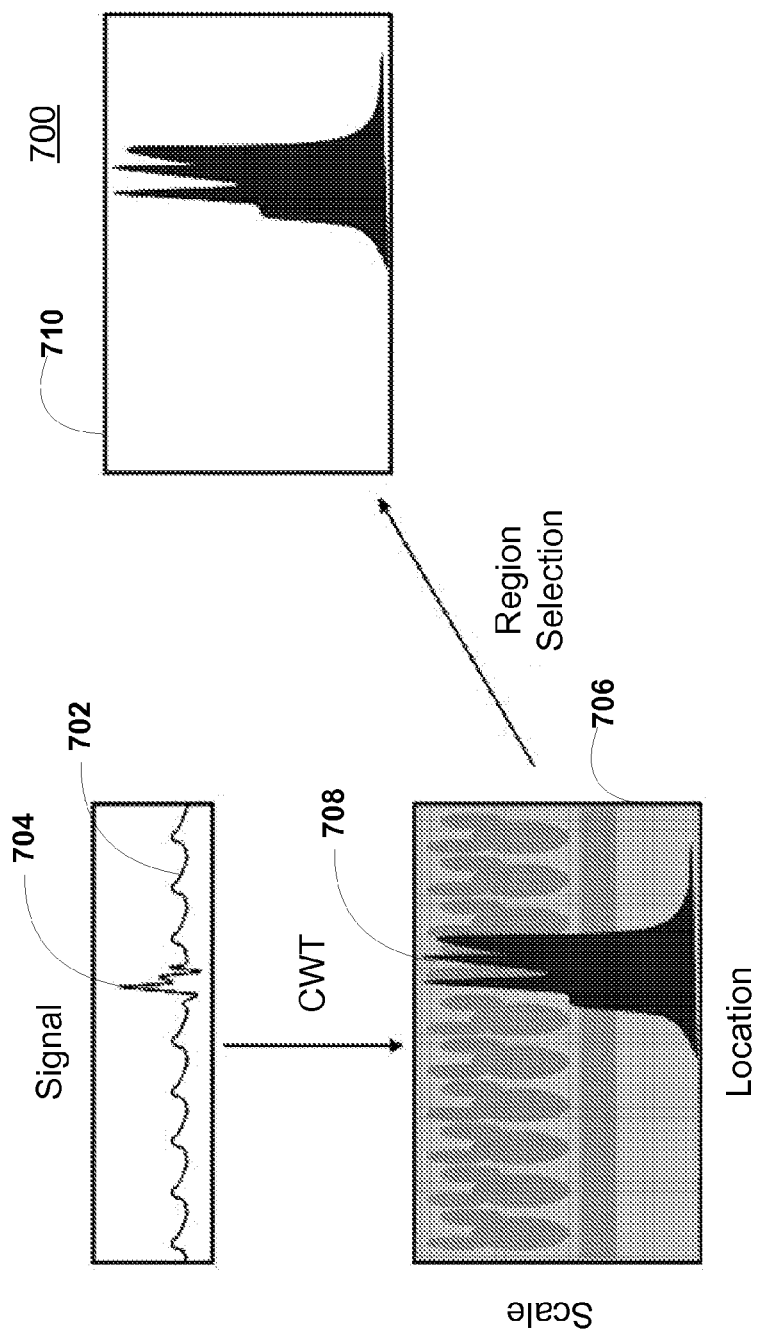
FIG. 7 shows an illustrative schematic of a system for generating a mask in accordance with an embodiment.

FIG. 7 illustrates process 700 in accordance with an embodiment of the present disclosure for generating a mask. For example, process 700 may be performed by wavelet processor 504 of FIG. 5 or processor 412 of FIG. 4. Signal 702 having noise 704 is transformed using a continuous wavelet transform, resulting in scalogram 706. Regions of resulting scalogram 706 that contain particular features (e.g., noise) may be identified. For example, region 708 which resulted from the continuous wavelet transform of noise 704 may be identified. Based on region 708, mask 710 may then be created. As mentioned above, the mask may be utilized to, for example, filter, zero out, smooth, replace, mark for later processing, ignore, or otherwise modify the identified noise regions. Additionally, an inverse continuous wavelet transform may be performed on the modified (or appropriately tagged) scalogram to generate a filtered signal.

Figure 8:
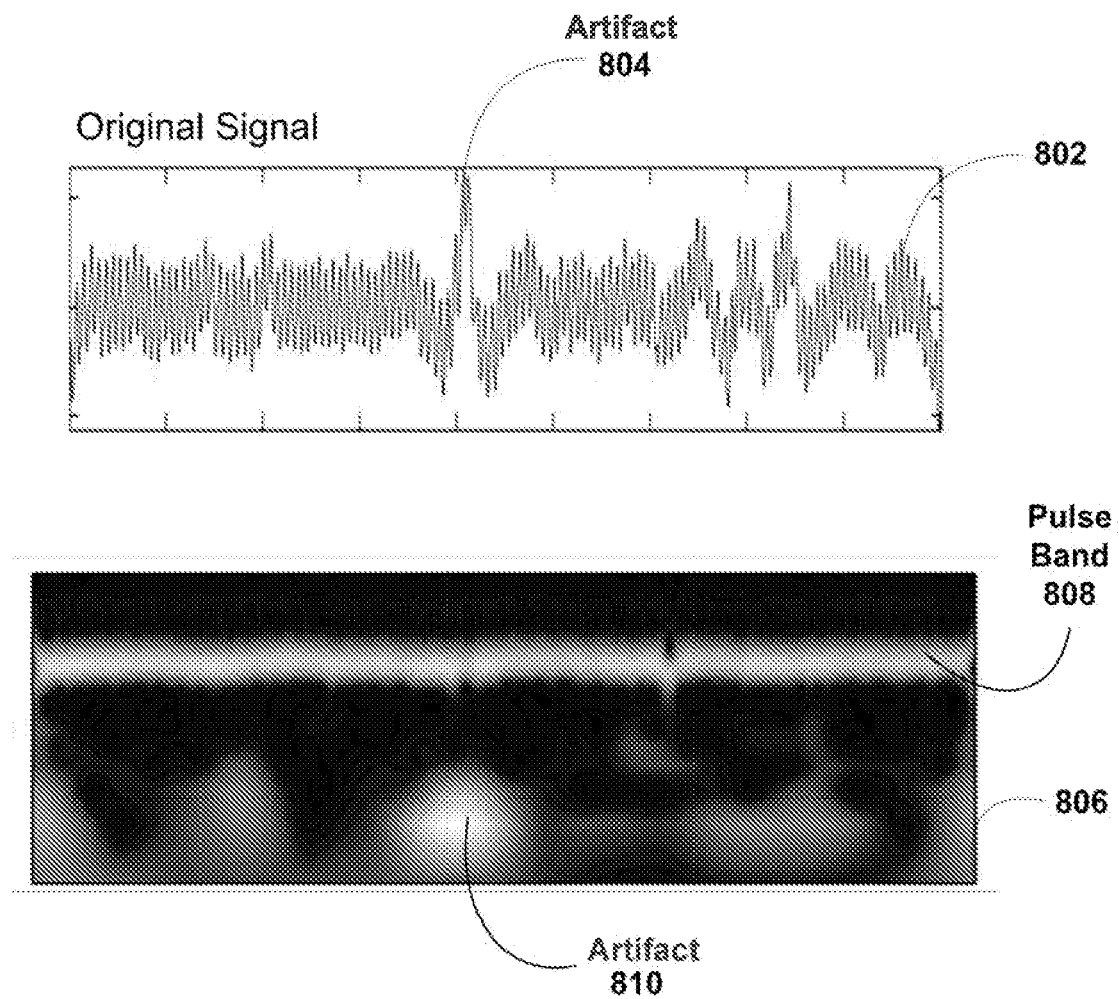
FIGS. 8 and 9 are illustrative examples of continuous wavelet filtering of a signal in accordance with an embodiment.
Figure 9:
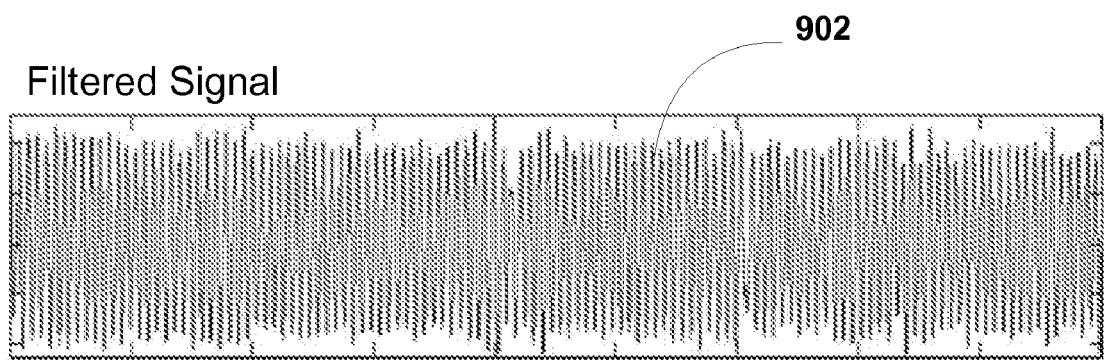

An example of continuous wavelet filtering of a PPG signal is shown in FIGS. 8 and 9. FIG. 8 shows a PPG signal 802 which may contain noise (e.g., artifact 804). A continuous wavelet transform of PPG signal 802 may then produce scalogram 806. Scalogram 806 clearly shows a high energy band 808 across the plot (higher energies are denoted by the lighter shades in the grayscale plot). This high energy band is caused by the pulse components in PPG signal 802 and is known as the "pulse band." Other features and/or higher energy regions may also be seen in scalogram 806. For example, artifact 810 appears in the lower region of scalogram 806. Artifact 810 corresponds to artifact 804 in the original PPG signal 802. This artifact 810 may be modified and/or marked (e.g., through the use of a mask) before performing an inverse wavelet transform of scalogram 806.

FIG. 9 illustrates an example in which artifact 810 of FIG. 8 is modified by setting the transform components in the locality of artifact 810 to zero prior to performing an inverse transform. Performing an inverse continuous wavelet transform on scalogram 806 after artifact 810 has been modified may then result in filtered signal 902. Comparing PPG signal 802 in FIG. 8 and filtered signal 902 in FIG. 9, it can be seen that regions of localized noise, such as artifact 804, have been filtered which may result in a significantly cleaner filtered signal 902. Filtered signal 902 may them be used in subsequent computations or provided for output on a display device.

Those skilled in the art will recognize that other forms of modification and masking of the selected transform components may be made, such as setting the selected components to a threshold value, or altering all the selected components by a factor.

It will be understood that the wavelet filtering techniques of the present disclosure may be practiced in combination with other known filtering techniques. For example, in one embodiment, an input signal may first be filtered to reduce noise using any suitable spectral domain techniques, adaptive filtering techniques, Kalman filtering, any other suitable filtering techniques, or any combination thereof. The filtered signal may then be further filtered using the wavelet techniques of the present disclosure.

Figure 10:
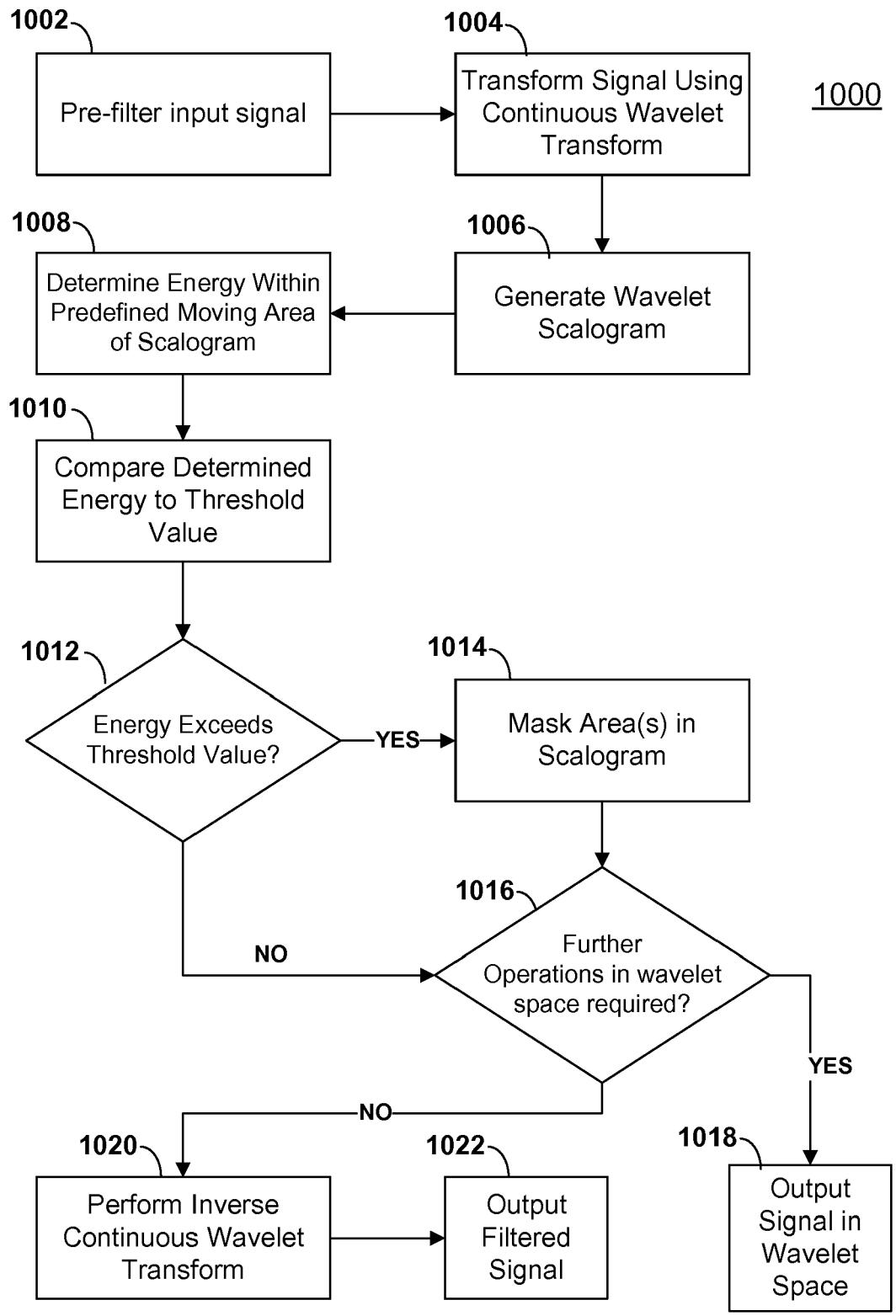
FIG. 10 shows an illustrative process for generating a filtered signal in accordance with an embodiment.

FIG. 10 shows illustrative process 1000 for identifying noise regions in a signal and generating a filtered signal. For example, process 1000 may illustrate steps 602, 604, 606, and 608 of FIG. 6 in more detail.

At step 1002, the input signal may be pre-filtered. For example, as mentioned above, pre-filtering may include any forms of filtering which are performed in addition to the wavelet filtering techniques of the present disclosure. Examples of pre-filtering include may be any suitable spectral domain techniques, adaptive filtering techniques, Kalman filtering, any other suitable filtering techniques, any combination thereof etc. However, one skilled in the art would appreciate that process 1000 may be modified, added to, and/or rearranged without departing from the scope of the disclosure. In particular, in an embodiment, step 1002 may be skipped and process 1000 may instead begin at step 1004.

At step 1004, a detected signal (e.g., a PPG signal) may be transformed using a continuous wavelet transform. For example, as described above, sensor 12 (FIG. 2) may detect a physiological signal (e.g., a PPG signal) from patient 40 (FIG. 2). Microprocessor 48 (FICA. 2), processor 412 (FIG. 4), and/or wavelet processor 504 (FIG. 5) may then compute the wavelet transform of the detected signal. In some embodiments, the wavelet transform may be performed by applying equation (9) to the detected signal.

At step 1006, a wavelet scalogram may be generated. For example, in some embodiments, microprocessor 48 (FIG. 2) or processor 412 (FIG. 4) may apply equation (10) to the continuous wavelet transform from step 1004 in order to produce a wavelet scalogram.

After the wavelet scalogram has been generated, at step 1008 the energy within one or more predefined moving areas of the wavelet scalogram may be determined. For example, in some embodiments, the energy within a generally wedge-shaped moving area may be computed by microprocessor 48 (FIG. 2) or processor 412 (FIG. 4) using, for example, equation (18). Because some types of noise in a wavelet scalogram may typically exhibit a generally wedge-shaped artifact area, computing the energy within a wedge-shaped area of the wavelet scalogram may enable more reliable noise detection for some types of noise.

At step 1010, the energy determined at step 1008 may be compared to a threshold energy level. The threshold energy level may be based, for example, on previously detected energy measurements (e.g., a running or moving average of previously detected energy measurements), the energy of the pulse band, a predetermined threshold, and/or any combination thereof. Furthermore, the threshold level may include both a local (derived from a short window) and global (derived from a larger window) component.

At step 1012, process 1000 may determine if determined energy at step 1008 exceeds the threshold level. For example, microprocessor 48 (FIG. 2) or processor 412 (FIG. 4) may determine if the determined energy exceeds the threshold level. In response to the determined energy exceeding the threshold value, process 1000 may proceed to step 1014 and these respective areas of the scalogram may be masked. As described in detail above, masking an area of the scalogram may include filtering, zeroing out, smoothing, replacing, marking for later processing, ignoring, or otherwise modifying the values in the scalogram area that were identified as exceeding the threshold value in step 1012.

After step 1014 or in response to the determined energy in the area of the scalogram not exceeding the threshold value in step 1012, process 1000 may then proceed to step 1016. In step 1016, process 1000 may determine if further operations in wavelet-space are required. If further options are required, then process 1000 may output the signal in wavelet space in step 1018.

However, if further options in wavelet-space are not required, then it may be beneficial to perform an inverse transform to remove the signal from wavelet-space. Thus, in response to further operations in wavelet-space not being required, an inverse wavelet transform may be performed in step 1020 and the resulting signal may be output as the filtered signal in step 1022. For example, in some embodiments, microprocessor 48 (FIG. 2) or processor 412 (FIG. 4) may apply equation (15) to the wavelet scalogram to perform the inverse wavelet transform.

In practice, one skilled in the art would appreciate that one or more steps shown in process 1000 may be combined with other steps, performed in any suitable order, performed in parallel (e.g., simultaneously or substantially simultaneously), or removed.

It will be understood that the foregoing is only illustrative of the principles of the disclosure, and that the disclosure can be practiced by other than the described embodiments, which are presented for purposes of illustration and not of limitation.

What is claimed is:

1. A method for filtering an input signal, the method comprising:
    performing, using processor circuitry, a continuous wavelet transform of an input signal to produce a transformed signal;
    generating a scalogram based, at least in part, on the transformed signal;
    identifying at least one region of noise in the scalogram based, at least in part, on a sliding-wedge window, wherein the sliding-wedge window analyzes wedge-shaped areas of the scalogram, wherein the wedge-shaped areas span a plurality of scales in the scalogram, and wherein the width of the wedge-shaped areas at a first of the plurality of scales is different than the width of the wedge-shaped areas at a second of the plurality of scales; and
    generating a filtered signal based, at least in part, on the at least one region of noise.

2. The method of claim 1, wherein generating a filtered signal comprises:
    tagging the at least one region of noise for later processing.

3. The method of claim 1, wherein generating a filtered signal comprises:

removing the at least one region of noise from the scalogram; and performing an inverse continuous wavelet transform on the scalogram.

4. The method of claim 3, wherein generating a filtered signal further comprises:

creating side skirts in the scalogram in an area surrounding the at least one region of noise.

5. The method of claim 1, further comprising:

identifying desired, non-noise components of the scalogram; and wherein generating a filtered signal comprises extracting the desired, non-noise components.

6. The method of claim 5, wherein identifying desired, non-noise components of the scalogram further comprises:

identifying particular regions of the scalogram that correspond to physiological operations in the input signal; and identifying the particular regions as desired components of the input signal.

7. A method for filtering an input signal, the method comprising:

performing, using processor circuitry, a continuous wavelet transform of an input signal to produce a transformed signal;

generating a scalogram based, at least in part, on the transformed signal;

identifying at least one region of noise in the scalogram based, at least in part, on a sliding-wedge window, wherein the sliding-wedge window analyzes wedge-shaped areas of the scalogram, and wherein identifying the at least one region of noise in the scalogram comprises:

comparing energy in a wedge-shaped area of the scalogram to a threshold value;

determining that the energy in the wedge-shaped area of the scalogram is greater than the threshold value; and identifying the wedge-shaped area of the scalogram as a region of noise in response to the determining: and generating a filtered signal based, at least in part, on the at least one region of noise.

8. A method of filtering an input signal, the method comprising:

performing, using processor circuitry, a continuous wavelet transform of an input signal to produce a transformed signal;

generating a scalogram based, at least in part, on the transformed signal;

identifying at least one region of noise in the scalogram;

identifying a repeating pattern in an area surrounding the at least one region of noise; and replacing values of the scalogram in the at least one region of noise with values that are consistent with the repeating pattern.

9. A system for filtering an input signal, the system comprising:

a sensor configured to detect an input signal; and a processor configured to:

perform a continuous wavelet transform of the input signal to produce a transformed signal;

generate a scalogram based, at least in part, on the transformed signal;

identify at least one region of noise in the scalogram based, at least in part, on a sliding-wedge window, wherein the sliding-wedge window analyzes wedge-shaped areas of the scalogram, wherein the wedge-shaped areas span a plurality of scales in the scalogram, and wherein the width of the wedge-shaped areas at a first of the plurality of scales is different than the width of the wedge-shaped areas at a second of the plurality of scales; and generate a filtered signal based, at least in part, on the at least one region of noise.

10. The system of claim 9, wherein the processor is further configured to:

tag the at least one region of noise for later processing.

11. The system of claim 9, wherein the processor is further configured to:

remove the at least one region of noise from the scalogram; and perform an inverse continuous wavelet transform on the scalogram.

12. The system of claim 11, wherein the processor is further configured to:

create side skirts in the scalogram in an area surrounding the at least one region of noise.

13. The system of claim 9, wherein the processor is further configured to:

identify desired, non-noise components of the scalogram; and extract the desired, non-noise components.

14. The system of claim 13, wherein the processor is further configured to:

identify particular regions of the scalogram that correspond to physiological operations in the input signal; and identify the particular regions as desired components of the input signal.

15. A system for filtering an input signal, the system comprising:

a sensor configured to detect an input signal; and a processor configured to:

perform a continuous wavelet transform of the input signal to produce a transformed signal;

generate a scalogram based, at least in part, on the transformed signal;

identify at least one region of noise in the scalogram based, at least in part, on a sliding-wedge window, wherein the sliding-wedge window analyzes wedge-shaped areas of the scalogram, and wherein the at least one region of noise is identified by:

comparing energy in a wedge-shaped area of the scalogram to a threshold value;

determining that the energy in the wedge-shaped area of the scalogram is greater than the threshold value; and identifying the wedge-shaped area of the scalogram as a region of noise in response to determining that the energy in the wedge-shaped area of the scalogram is greater than the threshold value: and generate a filtered signal based, at least in part, on the at least one region of noise.

16. A system for filtering an input signal, the system comprising:

a sensor configured to detect an input signal; and a processor configured to:

perform a continuous wavelet transform of the input signal to produce a transformed signal;

generate a scalogram based, at least in part, on the transformed signal;

identify at least one region of noise in the scalogram;

identify a repeating pattern in the scalogram in the area surrounding the at least one region of noise; and replace values of the scalogram in the at least one region of noise with values that are consistent with the repeating pattern.

17. A non-transitory computer-readable medium for use in filtering an input signal, the non-transitory computer-readable medium having computer program instructions recorded thereon for:
   performing a continuous wavelet transform of an input signal to produce a transformed signal;
   generating a scalogram based, at least in part, on the transformed signal;
   identifying at least one region of noise in the scalogram based, at least in part, on a sliding-wedge window, wherein the sliding-wedge window analyzes wedge-shaped areas of the scalogram, wherein the wedge-shaped areas span a plurality of scales in the scalogram, and wherein the width of the wedge-shaped areas at a first of the plurality of scales is different than the width of the wedge-shaped areas at a second of the plurality of scales; and
   generating a filtered signal based, at least in part, on the at least one region of noise.

18. A method for filtering an input signal, the method comprising:
   performing, using processor circuitry, a continuous wavelet transform of an input signal to produce a transformed signal;
   generating a scalogram based, at least in part, on the transformed signal;
   identifying at least one region of interest in the scalogram based, at least in part, on a sliding-wedge window, wherein the sliding-wedge window analyzes wedge-shaped areas of the scalogram, wherein the wedge-shaped areas span a plurality of scales in the scalogram, and wherein the width of the wedge-shaped areas at a first of the plurality of scales is different than the width of the wedge-shaped areas at a second of the plurality of scales; and
   performing an inverse continuous wavelet transform of the at least one region of interest.

* * * * *